(12) United States Patent
Li et al.

(10) Patent No.: US 10,765,327 B2
(45) Date of Patent: Sep. 8, 2020

(54) FINGER CUFF HAVING A SHELL

(71) Applicant: Edwards Lifesciences Corporation, Irvine, CA (US)

(72) Inventors: Peiyuan Li, Amsterdam (NL); Hendrik Petrus Van Der Weij, Helmund (NL); Jeroen Van Goudoever, Amstelveen (NL)

(73) Assignee: Edwards Lifesciences Corporation, Irvine, CA (US)

( * ) Notice: Subject to any disclaimer, the term of this patent is extended or adjusted under 35 U.S.C. 154(b) by 151 days.

(21) Appl. No.: 15/987,614

(22) Filed: May 23, 2018

(65) Prior Publication Data
US 2018/0353091 A1  Dec. 13, 2018

Related U.S. Application Data

(60) Provisional application No. 62/517,277, filed on Jun. 9, 2017.

(51) Int. Cl.
*A61B 5/022* (2006.01)
*A61B 5/0225* (2006.01)
*A61B 5/00* (2006.01)
*A61B 5/021* (2006.01)

(52) U.S. Cl.
CPC ...... *A61B 5/02241* (2013.01); *A61B 5/02141* (2013.01); *A61B 5/02255* (2013.01); *A61B 5/6826* (2013.01); *A61B 5/6838* (2013.01)

(58) Field of Classification Search
CPC ............ A61B 5/02241; A61B 5/02255; A61B 5/6826; A61B 5/6838; A61B 5/0245
See application file for complete search history.

(56) References Cited

U.S. PATENT DOCUMENTS

| | | | | |
|---|---|---|---|---|
| 4,202,347 A | * | 5/1980 | Sacks | A61B 5/02241 600/490 |
| 4,726,382 A | * | 2/1988 | Boehmer | A61B 5/02422 600/480 |
| 4,896,676 A | * | 1/1990 | Sasaki | A61B 5/02241 600/494 |
| 5,840,037 A | * | 11/1998 | Tochikubo | A61B 5/02233 600/499 |
| 7,524,291 B1 | | 4/2009 | Nakagawara | |

(Continued)

FOREIGN PATENT DOCUMENTS

| CN | 102688028 A | 9/2012 |
|---|---|---|
| WO | 2007041296 A1 | 4/2007 |

*Primary Examiner* — Tuan V Nguyen
(74) *Attorney, Agent, or Firm* — Eric King; Womble Bond Dickinson LLP

(57) ABSTRACT

Disclosed is finger cuff that is connectable to a patient's finger to aid in measuring the patient's blood pressure. The finger cuff may comprise: a shell, a bladder, and a clamping mechanism. The shell may have a finger cavity. The finger cavity of the shell may be placed under a patient's finger to receive the patient's finger. Further, the finger cavity may include a light emitting diode (LED)—photodiode (PD) pair. The bladder may include a pair of openings and the bladder may be mountable within the finger cavity such that the pair of openings surround the LED-PD pair, respectively. The clamping mechanism may be used to suitably clamp the patient's finger received in the finger cavity of the shell against the bladder mounted within the finger cavity of the shell.

24 Claims, 5 Drawing Sheets

(56) References Cited

U.S. PATENT DOCUMENTS

| | | | |
|---|---|---|---|
| 8,798,703 B2 | 8/2014 | Huber et al. | |
| 2003/0036690 A1* | 2/2003 | Geddes | A61B 5/02233 |
| | | | 600/323 |
| 2007/0021672 A1* | 1/2007 | Lee | A61B 5/02241 |
| | | | 600/499 |
| 2008/0058622 A1* | 3/2008 | Baker | A61B 5/14552 |
| | | | 600/344 |
| 2008/0076995 A1 | 3/2008 | Hoarau | |
| 2012/0059233 A1 | 3/2012 | Huber et al. | |

* cited by examiner

FINGER CUFF HAVING A SHELL

CROSS-REFERENCE TO RELATED APPLICATIONS

This application claims priority to U.S. Provisional Patent Application No. 62/517,277, filed Jun. 9, 2017, the contents of which is incorporated herein in its entirety.

BACKGROUND

Field

Embodiments of the invention may relate to a finger cuff having a shell.

Relevant Background

Volume clamping is a technique for non-invasively measuring blood pressure in which pressure is applied to a subject's finger in such a manner that arterial pressure may be balanced by a time varying pressure to maintain a constant arterial volume. In a properly fitted and calibrated system, the applied time varying pressure is equal to the arterial blood pressure in the finger. The applied time varying pressure may be measured to provide a reading of the patient's arterial blood pressure.

This may be accomplished by a finger cuff that is arranged around a finger of a patient. The finger cuff may include an infrared light source, an infrared sensor, and an inflatable bladder. The infrared light may be sent through the finger in which a finger artery is present. The infrared sensor picks up the infrared light and the amount of infrared light registered by the sensor may be inversely proportional to the artery diameter and indicative of the pressure in the artery.

In the finger cuff implementation, by inflating the bladder in the finger cuff, a pressure is exerted on the finger artery. If the pressure is high enough, it will compress the artery and the amount of light registered by the sensor will increase. The amount of pressure necessary in the inflatable bladder to compress the artery is dependent on the blood pressure. By controlling the pressure of the inflatable bladder such that the diameter of the finger artery is kept constant, the blood pressure may be monitored in very precise detail as the pressure in the inflatable bladder is directly linked to the blood pressure. In a typical present day finger cuff implementation, a volume clamp system is used with the finger cuff. The volume clamp system typically includes a pressure generating system and a regulating system that includes: a pump, a valve, and a pressure sensor in a closed loop feedback system that are used in the measurement of the arterial volume. To accurately measure blood pressure, the feedback loop provides sufficient pressure generating and releasing capabilities to match the pressure oscillations of the patient's blood pressure.

Today, many finger cuffs use a type of flexible band that wraps around a patient's finger and then utilize a conventional method to close or secure the finger cuff to the finger, such as, Velcro, or other securing means. Unfortunately, these types of finger cuffs are difficult to use by healthcare providers and also introduce attachment errors, such as, rotation errors, wrong orientation errors, lack of snugness errors, etc. These attachment errors then negatively impact the accuracy of the blood pressure measurement.

SUMMARY

Embodiments of the invention may relate to a finger cuff that is connectable to a patient's finger to aid in measuring the patient's blood pressure by a blood pressure measurement system. The finger cuff may comprise: a shell, a bladder, and a clamping mechanism. The shell may have a finger cavity and a pair of opposed first and second top portions. The finger cavity of the shell may be placed under a patient's finger to receive the patient's finger. Further, the finger cavity may include a light emitting diode (LED)—photodiode (PD) pair. The bladder may include a pair of openings and the bladder may be mountable within the finger cavity such that the pair of openings surround the LED-PD pair, respectively. The clamping mechanism may be coupled to the opposed first and second top portions of the shell. The clamping mechanism may be used to suitably clamp the patient's finger received in the finger cavity of the shell against the bladder mounted within the finger cavity of the shell, such that, the bladder and the LED-PD pair aid in measuring the patient's blood pressure by the blood pressure measurement system.

DETAILED DESCRIPTION

Figure 1:
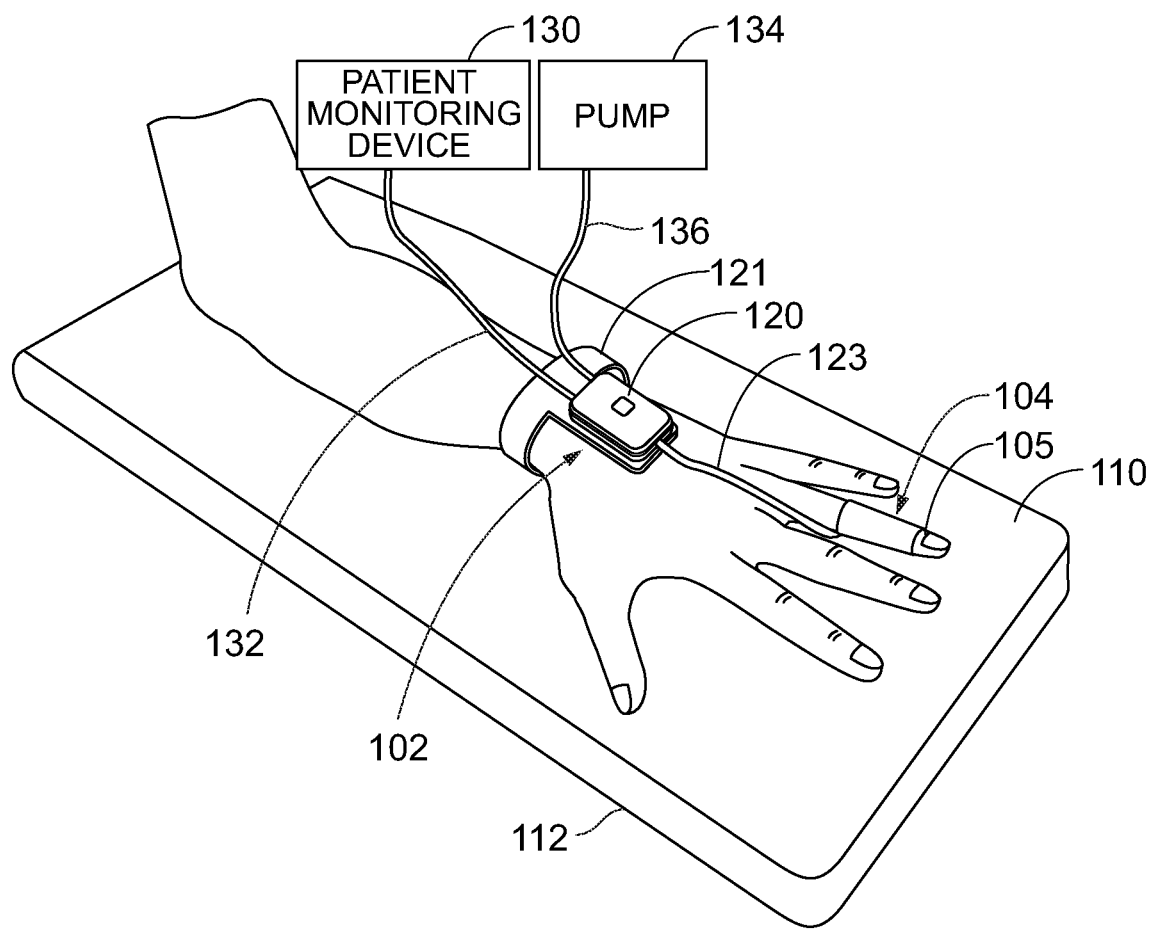
FIG. 1 is a diagram of an environment in which a finger cuff of a blood pressure measurement system may be implemented.

With reference to FIG. 1, an example of an environment in which a finger cuff 104 may be implemented will be described. As an example, a blood pressure measurement system 102 that includes a finger cuff 104 that may be attached to a patient's finger 105 and a blood pressure measurement controller 120 that may be attached to the patient's body (e.g., a patient's wrist or hand) is shown. The blood pressure measurement system 102 may further be connected to a patient monitoring device 130, and, in some embodiments, a pump 134. Further, finger cuff 104 may include a bladder (not shown) and an LED-PD pair (not shown), which are conventional for finger cuffs.

In one embodiment, the blood pressure measurement system 102 may include a pressure measurement controller 120 that includes: a small internal pump, a small internal valve, a pressure sensor, and control circuitry. In this embodiment, the control circuitry may be configured to: control the pneumatic pressure applied by the internal pump to the bladder of the finger cuff 104 to replicate the patient's blood pressure based upon measuring the pleth signal received from the LED-PD pair of the finger cuff 104. Further, the control circuitry may be configured to: control the opening of the internal valve to release pneumatic pressure; or the internal valve may simply be an orifice that is not controlled. Additionally, the control circuitry may be configured to: measure the patient's blood pressure by monitoring the pressure of the bladder based upon the input from a pressure sensor, which should be the same as patient's blood pressure, and may display the patient's blood pressure on the patient monitoring device 130.

In another embodiment, a conventional pressure generating and regulating system may be utilized, in which, a pump 134 is located remotely from the body of the patient. In this embodiment, the blood pressure measurement controller 120 receives pneumatic pressure from remote pump 134 through tube 136 and passes on the pneumatic pressure through tube 123 to the bladder of finger cuff 104. Blood pressure measurement device controller 120 may also control the pneumatic pressure (e.g., utilizing a controllable valve) applied to the finger cuff 104 as well as other functions. In this example, the pneumatic pressure applied by the pump 134 to the bladder of finger cuff 104 to replicate the patient's blood pressure based upon measuring the pleth signal received from the LED-PD pair of the finger cuff 104 and measuring the patient's blood pressure by monitoring the pressure of the bladder may be controlled by the blood pressure measurement controller 120 and/or a remote computing device and/or the pump 134 and/or the patient monitoring device 130. In some embodiments, a blood pressure measurement controller 120 is not used at all and there is simply a connection from the tube 123 to finger cuff 104 from a remote pump 134 including a remote pressure regulatory system, and all processing for the pressure generating and regulatory system, data processing, and display is performed by a remote computing device.

Continuing with this example, as shown in FIG. 1, a patient's hand may be placed on the face 110 of an arm rest 112 for measuring a patient's blood pressure with the blood pressure measurement system 102. The blood pressure measurement controller 120 of the blood pressure measurement system 102 may be coupled to a bladder of the finger cuff 104 in order to provide pneumatic pressure to the bladder for use in blood pressure measurement. Blood pressure measurement controller 120 may be coupled to the patient monitoring device 130 through a power/data cable 132. Also, in one embodiment, as previously described, in a remote implementation, blood pressure measurement controller 120 may be coupled to a remote pump 134 through tube 136 to receive pneumatic pressure for the bladder of the finger cuff 104. The patient monitoring device 130 may be any type of medical electronic device that may read, collect, process, display, etc., physiological readings/data of a patient including blood pressure, as well as any other suitable physiological patient readings. Accordingly, power/data cable 132 may transmit data to and from patient monitoring device 130 and also may provide power from the patient monitoring device 130 to the blood pressure measurement controller 120 and finger cuff 104.

As can be seen in FIG. 1, in one example, the finger cuff 104 may be attached to a patient's finger and the blood pressure measurement controller 120 may be attached on the patient's hand or wrist with an attachment bracelet 121 that wraps around the patient's wrist or hand. The attachment bracelet 121 may be metal, plastic, Velcro, etc. It should be appreciated that this is just one example of attaching a blood pressure measurement controller 120 and that any suitable way of attaching a blood pressure measurement controller to a patient's body or in close proximity to a patient's body may be utilized and that, in some embodiments, a blood pressure measurement controller 120 may not be used at all. It should further be appreciated that the finger cuff 104 may be connected to a blood pressure measurement controller described herein, or a pressure generating and regulating system of any other kind, such as a conventional pressure generating and regulating system that is located remotely from the body of the patient (e.g., a pump 134 located remotely from a patient). Any kind of pressure generating and regulating system that can be used, including but not limited to the blood pressure measurement controller, may be described simply as a pressure generating and regulating system. As a further example, in some embodiments, there may be no blood pressure measurement controller, at all, and a remote pump 134 that is controlled remotely may be directly connected via a tube 136 and 123 to finger cuff 104 to provide pneumatic pressure to the finger cuff 104.

In particular, as will be described in more detail hereafter, embodiments of the invention may relate to a finger cuff 104 that is connectable to a patient's finger 105 to aid in measuring the patient's blood pressure by the blood pressure measurement system 102. As will be described in more detail hereafter, the finger cuff 104 may comprise a shell, a bladder, and a clamping mechanism. The shell may have a finger cavity and a pair of opposed first and second top portions. The finger cavity of the shell may be placed under the patient's finger 105 to receive the patient's finger. The finger cavity may include a light emitting diode (LED)—photo diode (PD) pair (not shown). As will be described, the bladder (not shown) may include a pair of openings. The bladder may be mountable within the finger cavity such that the pair of openings surround the LED-PD pair, respectively. The clamping mechanism (not shown) may be coupled to the opposed first and second top portions of the shell. In particular, the clamping mechanism may be used to suitably clamp the patient's finger 105 received in the finger cavity of the shell against the bladder mounted within the finger cavity of the shell such that the bladder and the LED-PD pair aid in measuring the patient's blood pressure by the blood pressure measurement system 102 utilizing the volume clamping method.

With additional reference FIGS. 2A-2D, embodiments of the invention related to the shell finger cuff will be particularly described. As has been described, finger cuff 104 may be connectable to a patient's finger 105 to aid in measuring the patient's blood pressure by the previously described blood pressure measurement system 102 utilizing the volume clamping method. As can be seen in these figures, finger cuff 104 may particularly comprise: a shell 150; a bladder (as will be described in more detail hereafter); and a clamping mechanism 149.

Looking particularly at the shell 150, the shell 150 may be approximately arch-shaped and may have a finger cavity 151 and a pair of opposed first and second top portions 161. In particular, as can be seen in these figures, the finger cavity 151 of the shell 150 may be placed under a patient's finger 105 to receive the patient's finger 105 such that the half open shape formed by the shell 150 makes it easy to put the patient's finger in.

Figure 2A:
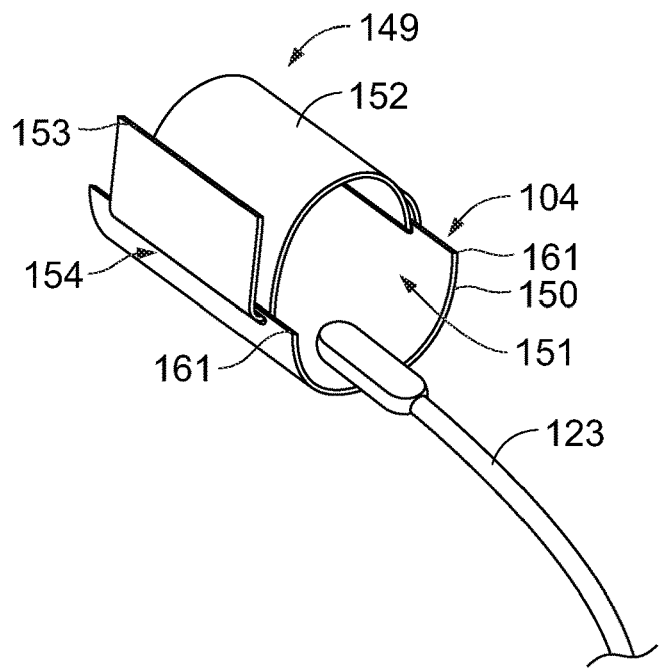
FIGS. 2A-2D are various views of finger cuff having a shell according to embodiments of the invention.
Figure 2B:
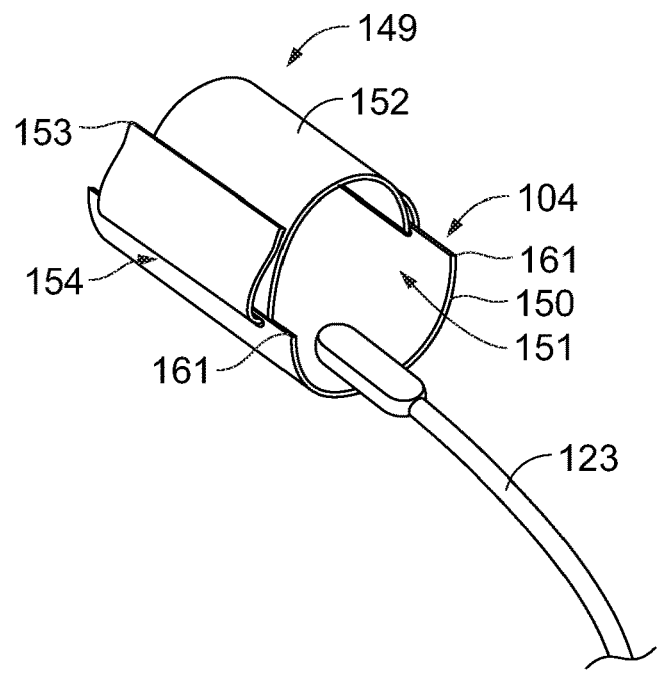
Figure 2C:
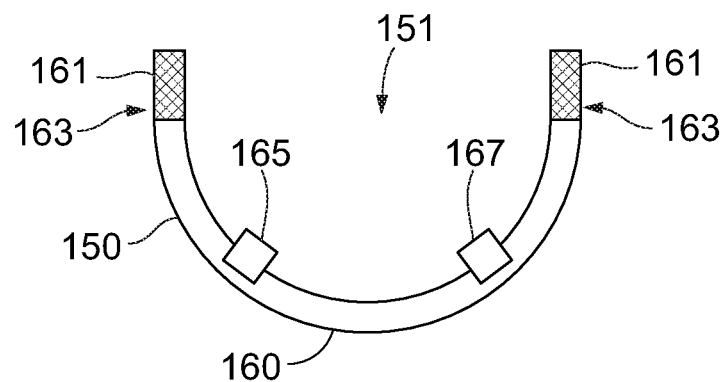
Figure 2D:
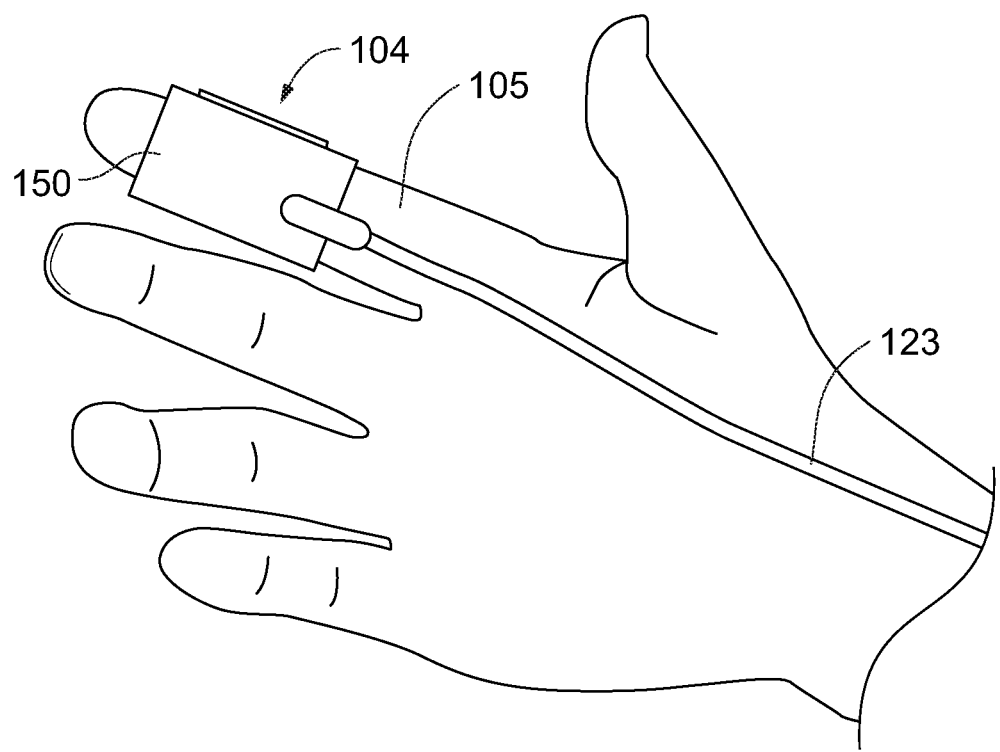

Also, the finger cavity 151 may include a LED-PD pair 165 and 167 (see particularly FIG. 2C). As will be described in more detail hereafter, the bladder may include a pair of openings such that the bladder may be mountable within the finger cavity 151, such that, the pair of openings surround the LED-PD pair 165 and 167. As can be particularly seen in FIG. 2C, in conjunction with FIGS. 2A, 2B, 2D, the shell 150 may include a lower section 160 that includes the LED-PD pair 165 and 167. This lower section 160 that includes the LED-PD pair 165 and 167 may be made from a more flexible material to provide flexibility in accommodating the patient's finger 105. Such type of flexible material may include a polyvinyl chloride (PVC) material or any suitably flexible material. It should be appreciated that the flexible material of the lower section 160, although flexible to accommodate the patient's finger, is rigid enough to form the cavity 151, when not in use. Also, the lower section 160 closely follows the lower side of the patient's finger reducing bladder volume which is beneficial for the servo performance of the volume clamp system. On the other hand, the shell 150 may also include a higher section 163 that includes the opposed first and second top portions 161. The opposed top portions 161 may be made of a more rigid material to accommodate the clamping mechanism 149, as will be described in more detail hereafter. It should be appreciated that any suitable sort of rigid material, such as, a metallic material, may be utilized.

Details of the clamping mechanism 149 will now be described in more detail with reference to FIGS. 2A-2D. In one embodiment, the clamping mechanism 149 may be coupled to the opposed first and second top portions 161 of the shell 150. The clamping mechanism 149 may be used to suitably clamp the patient's finger 105 received in the finger cavity 151 of the shell 150 against the bladder mounted within the finger cavity 151 such that the bladder and the LED-PD pair 165 and 167 may be used to aid in measuring the patient's blood pressure by the blood pressure measurement system 102 utilizing the volume clamping method.

In one particular embodiment, the clamping mechanism 149 may include a pulling and closing mechanism that comprises a flexible material 152 having a first end and a second end. In one embodiment, the flexible material 152 may be considered a flap or a strap. The first end of the flexible material 152 may be permanently mounted to the first top portion 161 of the shell 150. For example, the flexible material 152 may be mounted to a first slot of the first top portion 161 of the shell 150. Further, the second end 153 of the flexible material 152 may be extendable through a second slot 154 of the second top portion 161 of the shell 150 such that the second end 153 may be pulled by a healthcare provider through the second slot 154 such that the flexible material 152 clamps the patient's finger 105 securely within the finger cavity 151 of the shell 150. It should be appreciated that the slots are formed in the opposed rigid top sections 161 to provide strength for the clamping mechanism. Further, thereafter, a bottom portion of the flexible material 152 near the second end 153 may be affixed to a remainder of the flexible material 152 (e.g., on the top of the flexible material 152) such that the flexible material 152 is locked in place and secures the patient's finger 105 within the finger cuff 104 for more accurate blood pressure measurements. As an example, Velcro portions on the bottom portion of the flexible material 152 near the second end 153 and on the top portion of the flexible material 152 may connect together to lock the flexible material in place (e.g., see FIGS. 2A and 2B). In this way, a tight fit of the finger 105 to the finger cuff 104 is ensured. Also, by having a tight fit with the clamping mechanism 149, the air pressure from the bladder is efficiently transferred to the finger artery. Also, although a Velcro implementation is provided as an example to lock the flexible material 152 in place, it should be appreciated that other affixing means may be utilized such as glue, tape, adhesives, etc.

In particular, by utilizing the shell 150 that extends around a patient's finger 105, that guides the finger 105 in, and, that, is then secured in place by the clamping mechanism 149, such that a snug fit is provided, orientation and rotation errors due to the movement of the finger are avoided, and more accurate blood pressure measurements can be taken by the volume clamp method of the blood pressure measurement system 102. In particular, with the clamping mechanism 149 firmly clamping the patient's finger 105 received in the finger cavity 151 of the shell 150 against the bladder mounted within the finger cavity 151 of the shell 150, the bladder (being provided pneumatic pressure through the tube 123) and the LED-PD pair 165 and 167, may be more accurately utilized in measuring the patient's blood pressure by the volume clamp method of the blood pressure measurement system 102. Additionally, the shell 150 being formed with a rigid higher section and a more flexible lower section may be molded such that it is efficient to manufacture and easy to mount the optical components and bladder to the lower section.

Figure 3A:
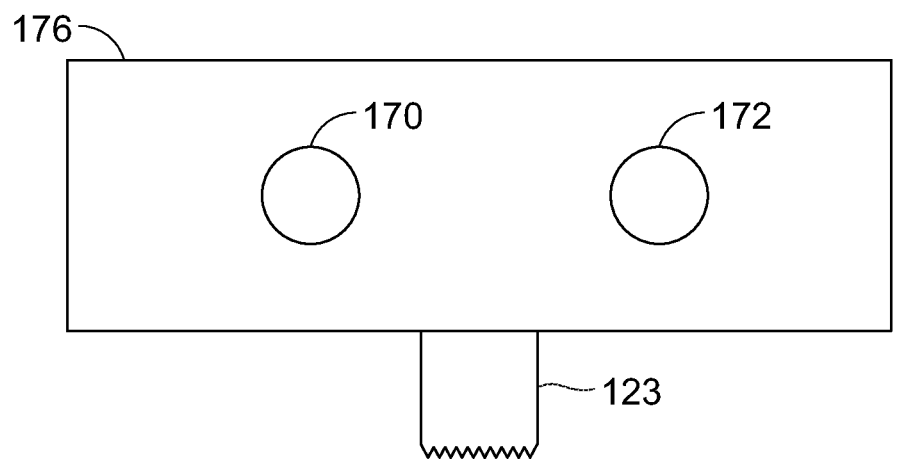
FIGS. 3A-3B are various views of a bladder that may be utilized with the finger cuff having a shell according to embodiments of the invention.
Figure 3B:
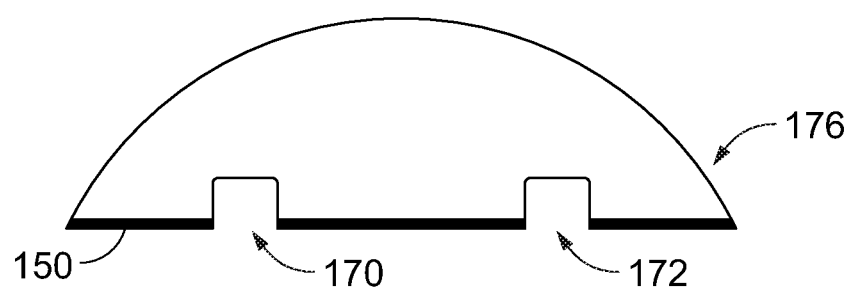

With additional reference FIGS. 3A and 3B, in one embodiment, a bladder 176 that is fully inflatable may be utilized. Bladder 176 may be connected to tube 123 for receiving pneumatic pressure. Further, bladder 176 may include a pair of circular openings 170 and 172 such that bladder 176 may be mounted within the finger cavity 151 to the shell 150 such that the pair of openings 170 and 172 surround the LED-PD pair 165 and 167, respectively. Thus, the two openings 170 and 172 particularly align and surround the LED-PD pair 165 and 167 to allow for the bladder to inflate and deflate within the finger cavity 151 of the shell 150. Also, this type of bladder 176 provides a full volume of air, as shown in FIG. 3B, which is a more efficient implementation of air volume than previous types of bladders. As has been described, with the clamping mechanism 149 firmly clamping the patient's finger 105 received in the finger cavity 151 of the shell 150 against the bladder 176 mounted within the finger cavity 151 of the shell 150, the bladder 176 and the LED-PD pair 165 and 167 may be more accurately utilized in measuring the patient's blood pressure by the volume clamp method of the blood pressure measurement system 102.

It should be appreciated that the shell 150, the LED-PD pair 165 and 167, and the clamping mechanism 147 of the finger cuff 104 may be re-usable. Further, although bladder 176 may also be re-usable it may also be disposable and replaceable. Thus, in one embodiment, bladder 176 is disposable and replaceable such that a new bladder 176 may be mountable within the finger cavity 151 of the shell 150 of the finger cuff 104 so that the pair of openings 170 and 172 surround the LED-PD pair 165 and 167, respectively. Thus, in some embodiments, the shell 150 and clamping mechanism 149 of finger cuff 104 are re-usable and the bladder 176 may be disposable and replaceable. By utilizing this type of disposable and replaceable implementation of the bladder 176 with the re-usable finger cuff 104 (shell 150 and clamping mechanism 149), significant cost savings may be realized due to the fact that the key components of the finger cuff 104 are not completely disposable and may be re-used. In fact, the main components of the finger cuff 104—the shell 150, the LED-PD pair 165 and 167, and the clamping mechanism 149, are all re-usable and only the bladder 176 is disposable.

Figure 4:
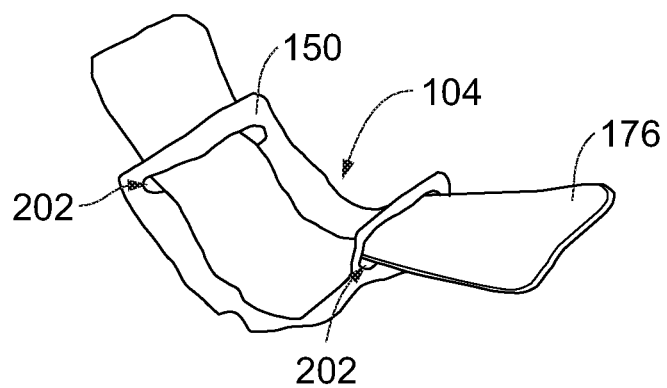
FIG. 4 is a view of a diagram illustrating a disposable bladder that is connectable to a shell of the finger cuff according to embodiments of the invention.

With brief additional reference to FIG. 4, in one embodiment, the bladder 176 may be mounted within the finger cavity 151 of the shell 150 of the finger cuff 104 such that the pair of openings 170 and 172 surround the LED-PD pair 165 and 167 to aid in measuring the patient's blood pressure by the blood pressure measurement system, as has been previously described. Further, in one embodiment, the bladder 176 may extend through slots 202 of the shell 150 of the finger cuff 104 to aid in the easy attachment and removal of the bladder 176 to the finger cuff 104. This approach may aid in the ease of utilizing a disposable bladder 176 to a re-usable solid finger cuff 104 (e.g., utilizing the shell 150 and clamping mechanism). It should be appreciated that this is just one example of attaching a disposable bladder 176 to a re-usable solid finger cuff 104 and that many other techniques may be utilized.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A finger cuff connectable to a patient's finger to aid in measuring the patient's blood pressure by a blood pressure measurement system, the finger cuff comprising:
    a shell having a finger cavity and a pair of opposed first and second top portions, the finger cavity of the shell placed under a patient's finger to receive the patient's finger, the finger cavity including a light emitting diode (LED)—photodiode (PD) pair, wherein the shell is fixed thereby not including rotatable sections;
    a bladder including a pair of openings, the bladder mountable within the finger cavity such that the pair of openings surround the LED-PD pair, respectively; and
    a clamping mechanism coupled to the opposed first and second top portions of the shell, the clamping mechanism to suitably clamp the patient's finger received in the finger cavity of the shell against the bladder mounted within the finger cavity of the shell such that the bladder and the LED-PD pair aid in measuring the patient's blood pressure by the blood pressure measurement system.

2. The finger cuff of claim 1, wherein the shell is approximately arch-shaped and includes a lower section and a higher section.

3. The finger cuff of claim 2, wherein the lower section includes the LED-PD pair and includes a flexible material.

4. The finger cuff of claim 2, wherein the higher section includes the opposed first and second top portions and includes a rigid material.

5. The finger cuff of claim 4, wherein the clamping mechanism includes a pulling and closing mechanism that comprises a flexible material having a first end and a second end, the first end of the flexible material permanently mounted to a first slot of the first top portion and the second end of the flexible material being extendable through a second slot of the second top portion such that the second end may be pulled through the second slot such that flexible material clamps the patient's finger securely within the finger cavity of the shell and thereafter the second end is affixed to a remainder of the flexible material to be locked in place.

6. The finger cuff of claim 1, wherein the shell and clamping mechanism are re-usable.

7. The finger cuff of claim 6, wherein the bladder is re-usable.

8. The finger cuff of claim 6, wherein the bladder is disposable and replaceable such that a new bladder is mountable within the finger cavity of the shell so that the pair of openings surround the LED-PD pair, respectively.

9. A method to attach a finger cuff including a shell having a finger cavity and a clamping mechanism that is coupled to opposed first and second top portions of the shell by a healthcare provider to a patient's finger to aid in measuring the patient's blood pressure by a blood pressure measurement system, the finger cavity including a light emitting diode (LED)—photodiode (PD) pair and a bladder mounted in the finger cavity, the bladder including a pair of openings that surround the LED-PD pair, respectively, the method comprising:

placing the finger cavity of the shell of the finger cuff under the patient's finger to receive the patient's finger, wherein the shell is fixed thereby not including rotatable sections; and
clamping the patient's finger received in the finger cavity of the shell against the bladder mounted within the finger cavity of the shell with the clamping mechanism such that the bladder and the LED-PD pair aid in measuring the patient's blood pressure by the blood pressure measurement system.

10. The method claim 9, wherein the shell is approximately arch-shaped and includes a lower section and a higher section.

11. The method claim 10, wherein the lower section includes the LED-PD pair and includes a flexible material.

12. The method claim 10, wherein the higher section includes the opposed first and second top portions and includes a rigid material.

13. The method claim 12, wherein the clamping mechanism includes a pulling and closing mechanism that comprises a flexible material having a first end and a second end, the first end of the flexible material permanently mounted to a first slot of the first top portion and the second end of the flexible material being extendable through a second slot of the second top portion such that the second end may be pulled through the second slot by the healthcare provider such that flexible material clamps the patient's finger securely within the finger cavity of the shell and thereafter the second end is affixed to a remainder of the flexible material to be locked in place by the healthcare provider.

14. The method claim 9, wherein the shell and clamping mechanism are re-usable.

15. The method claim 14, wherein the bladder is re-usable.

16. The method claim 14, wherein the bladder is disposable and replaceable such that a new bladder is mountable within the finger cavity of the shell so that the pair of openings surround the LED-PD pair, respectively.

17. A blood pressure measurement system to measure a patient's blood pressure utilizing volume clamping comprising:
    a finger cuff connectable to a patient's finger, the finger cuff comprising:
        a shell having a finger cavity and a pair of opposed first and second top portions, the finger cavity of the shell placed under a patient's finger to receive the patient's finger, the finger cavity including a light emitting diode (LED)—photodiode (PD) pair, wherein the shell is fixed thereby not including rotatable sections;
        a bladder including a pair of openings, the bladder mountable within the finger cavity such that the pair of openings surround the LED-PD pair, respectively; and
        a clamping mechanism coupled to the opposed first and second top portions of the shell, the clamping mechanism to suitably clamp the patient's finger received in the finger cavity of the shell against the bladder mounted within the finger cavity of the shell such that the bladder and the LED-PD pair aid in measuring the patient's blood pressure by the blood pressure measurement system utilizing volume clamping.

18. The blood pressure measurement system of claim 17, wherein the shell is approximately arch-shaped and includes a lower section and a higher section.

19. The blood pressure measurement system of claim 18, wherein the lower section includes the LED-PD pair and includes a flexible material.

20. The blood pressure measurement system of claim 18, wherein the higher section includes the opposed first and second top portions and includes a rigid material.

21. The blood pressure measurement system of claim 20, wherein the clamping mechanism includes a pulling and closing mechanism that comprises a flexible material having a first end and a second end, the first end of the flexible material permanently mounted to a first slot of the first top portion and the second end of the flexible material being extendable through a second slot of the second top portion such that the second end may be pulled through the second slot such that flexible material clamps the patient's finger securely within the finger cavity of the shell and thereafter the second end is affixed to a remainder of the flexible material to be locked in place.

22. The blood pressure measurement system of claim 17, wherein the shell and clamping mechanism are re-usable.

23. The blood pressure measurement system of claim 22, wherein the bladder is re-usable.

24. The blood pressure measurement system of claim 22, wherein the bladder is disposable and replaceable such that a new bladder is mountable within the finger cavity of the shell so that the pair of openings surround the LED-PD pair, respectively.

\* \* \* \* \*